United States Patent [19]

Jeschke et al.

[11] Patent Number: 5,428,049
[45] Date of Patent: Jun. 27, 1995

[54] INSECTICIDAL AND ACARICIDAL PLANT-PROTECTION AGENTS CONTAINING SUBSTITUTED 1,2,4-OXADIAZOLE DERIVATIVES

[75] Inventors: Peter Jeschke, Leverkusen; Werner Lindner, Cologne; Ulrike Wachendorff-Neumann, Monheim; Christoph Erdelen, Leichlingen, all of Germany

[73] Assignee: Bayer Aktiengesellschaft, Leverkusen, Germany

[21] Appl. No.: 182,124

[22] PCT Filed: Jul. 6, 1992

[86] PCT No.: PCT/EP92/01525

§ 371 Date: Jan. 13, 1994

§ 102(e) Date: Jan. 13, 1994

[87] PCT Pub. No.: WO93/01719

PCT Pub. Date: Feb. 4, 1993

[30] Foreign Application Priority Data

Jul. 20, 1991 [DE] Germany ............ 41 24 151.7

[51] Int. Cl.⁶ ............... C07D 271/06; A01N 43/82
[52] U.S. Cl. ............................. 514/364; 548/131
[58] Field of Search ................ 548/131; 514/364

[56] References Cited

U.S. PATENT DOCUMENTS

| | | | |
|---|---|---|---|
| 3,192,103 | 6/1965 | Sousa et al. | 514/365 |
| 4,012,377 | 3/1977 | Claisse et al. | 514/365 |

FOREIGN PATENT DOCUMENTS

| | | |
|---|---|---|
| 0036711 | 9/1981 | European Pat. Off. |
| 0074079 | 3/1983 | European Pat. Off. |
| 0273534 | 7/1988 | European Pat. Off. |
| 0492249 | 7/1992 | European Pat. Off. |
| 2426878 | 1/1976 | Germany |

OTHER PUBLICATIONS

Chemical Abstract, vol. 109, 1988, p. 18; CA# 142067v: "Action of potent cholinergic anthlemintics...", R. D. Pinnock, et al.

J. C. S. Perkin I, pp. 2241–2249, Nov. 29, 1972; "Some 5-Unsubstituted Acetylenic and Vinylic 1,2,4-Oxadiazoles", J. A. Claisse et al.

*Primary Examiner*—Robert Gerstl
*Attorney, Agent, or Firm*—Sprung Horn Kramer & Woods

[57] ABSTRACT

The present invention relates to the use of 1,2,4-oxadiazole derivatives, some of which are already known, as insecticides and acaricides in plant protection.

The compounds, used in accordance with the invention, have the formula (I)

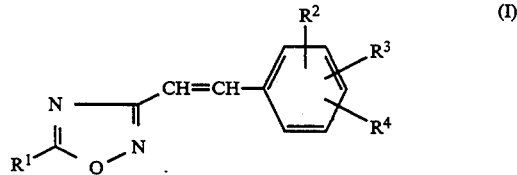

in which $R^1$ represents hydrogen, or represents in each case optionally substituted alkyl, cycloalkyl, aryl or heterocyclyl, $R^2$ represents hydrogen, nitro, cyano, carboxyl, carbamoyl or halogen, or represents in each case optionally substituted alkyl, alkoxy or alkylthio, $R^3$ represents hydrogen, nitro, cyano, carboxyl, carbamoyl or halogen, or represents in each case optionally substituted alkyl, alkoxy or alkylthio, and $R^4$ has the meaning given in the text of the application.

3 Claims, No Drawings

INSECTICIDAL AND ACARICIDAL PLANT-PROTECTION AGENTS CONTAINING SUBSTITUTED 1,2,4-OXADIAZOLE DERIVATIVES

This application is a 371 PCT/EP92/01525 Jul. 6, 1992.

The present invention relates to the use of 1,2,4-oxadiazole derivatives, some of which are already known, as insecticides and acaricides in plant protection.

It is already known that certain 1,2,4-oxadiazole derivatives possess parasiticidal (in particular endoparasiticidal) activity in humans and animals (cf. U.S. Pat. No. 4,012,377).

Certain 1,2,4-oxadiazole derivatives and their use as endoparasiticides are the subject-matter of an older, but not previously published, patent application (cf. German patent application No. 4041474 of 22.12.1990).

It has now been found that the 1,2,4-oxadiazole derivatives, some of which are already known, of the general formula (I)

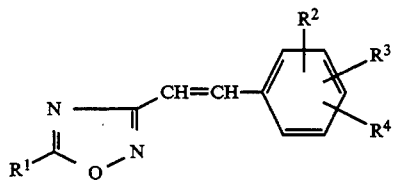

in which
- $R^1$ represents hydrogen, or represents in each case optionally substituted alkyl, cycloalkyl, aryl or heterocyclyl,
- $R^2$ represents hydrogen, nitro, cyano, carboxyl, carbamoyl or halogen, or represents in each case optionally substituted alkyl, alkoxy or alkylthio,
- $R^3$ represents hydrogen, nitro, cyano, carboxyl, carbamoyl or halogen, or represents in each case optionally substituted alkyl, alkoxy or alkylthio, and
- $R^4$ represents hydrogen, hydroxyl, mercapto, amino, halogen, alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, alkylamino, dialkylamino, alkylcarbonylamino, alkylcarbonyl, alkylcarbonyloxy, alkoxycarbonyl, alkoxyalkyl, hydroxyalkoxy or alkoxyalkoxy, or represents aryl, aryloxy, aralkyloxy, arylthio, aralkylthio, arylsulphinyl or arylsulphonyl, which are in each case optionally substituted by halogen, alkyl, halogenoalkyl, alkoxy or halogenoalkoxy, or, together with $R^3$, represents alkanediyl, alkylene(di)oxy or halogenoalkylenedioxy, exhibit strong activity against plant-parasitic insects and mites.

The substituted 1,2,4-oxadiazole derivatives, to be used in accordance with the invention, are generally defined by the formula (I). In accordance with the invention, those compounds of the formula (I) are preferably used in which
- $R^1$ represents hydrogen, or represents straight-chain or branched alkyl having 1 to 6 carbon atoms, which is optionally substituted by hydroxyl, halogen, $C_3$-$C_6$-cycloalkyl, $C_1$-$C_6$-alkoxy, $C_1$-$C_4$-alkyl-carbonyl, $C_1$-$C_4$-alkoxy-carbonyl or phenyl, or represents $C_3$-$C_6$-cycloalkyl or phenyl, which are in each case optionally substituted by halogen or $C_1$-$C_4$-alkyl, or represents pyridyl, furyl or thienyl,
- $R^2$ represents hydrogen, nitro, cyano, carboxyl, carbamoyl or halogen, or represents alkyl, alkoxy or alkylthio having in each case 1 to 4 carbon atoms, which are in each case optionally substituted by halogen,
- $R^3$ represents hydrogen, nitro, cyano, carboxyl, carbamoyl or halogen, or represents alkyl, alkoxy or alkylthio having in each case 1 to 4 carbon atoms, which are in each case optionally substituted by halogen, and
- $R^4$ represents hydrogen, hydroxyl, mercapto, amino or halogen, or represents alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, alkylamino, dialkylamino, alkylcarbonylamino, alkylcarbonyl, alkylcarbonyloxy, alkoxycarbonyl, alkoxyalkyl, hydroxyalkoxy or alkoxyalkoxy having in each case 1 to 4 carbon atoms, or represents phenyl, phenoxy, benzyloxy, phenylthio, benzylthio, phenylsulphinyl or phenylsulphonyl, which are in each case optionally substituted by halogen, $C_1$-$C_4$-alkyl, $C_1$-$C_4$-halogenoalkyl, $C_1$-$C_4$-alkoxy or $C_1$-$C_4$-halogenoalkoxy, or, together with $R^3$, represents $C_3$-$C_4$-alkanediyl, $C_1$-$C_3$-alkylene(di)oxy or $C_1$-$C_2$-halogenoalkylenedioxy.

In accordance with the invention, those compounds of the formula (I) are used in particular in which
- $R^1$ represents hydrogen, or represents straight-chain or branched $C_1$-$C_4$-alkyl, which is optionally substituted by fluorine, chlorine, bromine, methoxy, ethoxy, acetyl, propionyl, methoxycarbonyl or ethoxycarbonyl, or represents cyclopropyl, cyclopentyl, cyclohexyl or thienyl,
- $R^2$ represents hydrogen, nitro, cyano, fluorine, chlorine or bromine, or represents alkyl, alkoxy or alkylthio having in each case 1 to 4 carbon atoms, which are in each case optionally substituted by fluorine and/or chlorine,
- $R^3$ represents hydrogen, nitro, cyano, fluorine, chlorine or bromine, or represents alkyl having 1 to 4 carbon atoms, which is in each case optionally substituted by fluorine and/or chlorine, and
- $R^4$ represents hydrogen, fluorine, chlorine, bromine, methyl, ethyl, trifluoromethyl, chlorodifluoromethyl, fluorodichloromethyl, methoxy, ethoxy, difluoromethoxy, trifluoromethoxy, methylthio, ethylthio, difluoromethylthio, trifluoromethylthio, chlorodifluoromethylthio, fluorodichloromethylthio, methylsulphinyl, ethylsulphinyl, trifluoromethylsulphinyl, methylsulphonyl, ethylsulphonyl, trifluoromethylsulphonyl, methylamino, ethylamino, dimethylamino, acetylamino, acetyl, acetyloxy, methoxycarbonyl or ethoxycarbonyl, or represents phenyl, phenoxy or benzyloxy, which are in each case optionally substituted by fluorine, chlorine, bromine, methyl, trifluoromethyl, methoxy or trifluoromethoxy, or, together with $R^3$, represents $C_1$-$C_2$-alkylenedioxy which is optionally substituted by fluorine and/or chlorine.

In accordance with the invention, all forms of the compounds of the formula (I) exhibiting configurational isomerism with regard to the olefinic double bond (E and Z isomers), and mixtures thereof, may be used.

Preferably, however, the E isomers of the compounds of the formula (I) are used according to the invention.

The substituted 1,2,4-oxadiazole derivatives which are to be used according to the invention are known and/or can be prepared by processes which are known per se (cf. U.S. Pat. No. 4,102,377; J. Chem. Soc. 1973, 2241-2249; German Patent Application No. 4041474).

The compounds of the formula (I) are obtained if amide oximes of the formula (II)

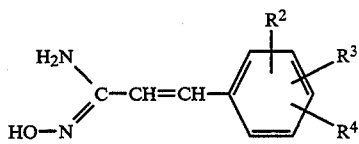

in which

R$^2$, R$^3$ and R$^4$ have the abovementioned meanings, are reacted with carboxylic acid derivatives of the formulae (III), (IV), (V) or (VI)

 (III)

 (IV)

 (V)

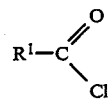 (VI)

in which

R$^1$ has the abovementioned meaning and

R represents methyl or ethyl, optionally in the presence of a reaction aid, such as, for example, boron trifluoride etherate or pyridine, and optionally in the presence of a diluent, such as, for example, chlorobenzene or chloroform, at temperatures between 10° C. and 180° C., and are worked up in accordance with customary methods (cf. the Preparation Examples).

The amide oximes of the formula (II) are known and/or can be prepared by processes which are known per se (cf. J. Chem. Soc. Perkin I 1973, 2241-2249; J. Heterocycl. Chem. 15 (1978), 1373-1378).

The carboxylic acid derivatives of the formulae (III), (IV), (V) and (VI) are known organic chemicals used in synthesis.

The compounds of the formula (I) are suitable for controlling animal pests in plant cultivation, in particular insects and mites. They are active against normally sensitive and resistant species and against all or individual stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and *Scutigera spec.*

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp..

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanierum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata luens, Aonidiella aurantii, Aspidiotus hederae,* Pseudococcus spp. and Psylla spp.

From the order of the Lepidoptera, for example, *Pectinophora ossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Arotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punttatum, Rhizopertha dominica, Acanthoscelides obtectus, Acanthoscelides obtectus, Hylotrupes bajulus, Aelastica alni, Leptinotarsa decemlineata, Phaedon cochleariae,* Diabrotica spp., *Psylliodes chrysocephala, Epilachna varive stis,* Atomaria spp., *Oryzaephilus surinamensis, Antho nomus* spp., Sitophilus spp., *Otiorrhynchus sulcatus, Cosmopolites sordidus, Ceuthorrhynchus assimilis, Hypera postica,* Dermestes spp., Trooderma spp., Anthrenus spp., Attagenus spp., Lyctus spp., *Meliethes aeneus,* Ptinus spp., *Niptus hololeucus, Gibbiumpsyiloides,* Tribolium spp., *Tenebrio molitor,* Agriotes spp., Cono derus spp., *Melolontha melolontha, Amphimallon solsti tialis* and *Costelytra zealandica*.

From the order of the Hymenoptera, for example, Diprion spp., Hoplocampa spp., nasius spp., *Monomorium pharaonis* and Vespa spp.

From the order of the Diptera, for example, Aedes spp., Anopheles spp., Culex spp., *Drosophila mela-* noaster, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp..

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp..

Depending on their particular physical and/or chemical properties, the active compounds can be converted to the customary formulations, such as solutions, emulsions, suspensions, powders, foams, pastes, granules, aerosols, natural and synthetic substances impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone; methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds can be present both in their commercially available formulations and in the use forms prepared from these formulations mixed with other active compounds, such as insecticides, attractants, sterilants, acaricides, nematicides, fungicides, growth-regulating compounds or herbicides. The insecticides include, for example, phosphoric acid esters, carbamates, carboxylic acid esters, chlorinated hydrocarbons, phenylureas and compounds produced by microorganisms, inter alia.

In addition, the active compounds can be present both in their commercially available formulations and in the use forms prepared from these formulations mixed with synergists. Synergists are compounds through which the effect of the active compounds is increased without the added synergist itself having to be active.

The content of active compound in the use forms prepared from the commercially available formulations can vary over wide ranges. The concentration of active compound in the use forms can be from 0.0000001 up to 95% by weight of active compound, preferably between 0.0001 and 1% by weight.

The active compounds are used in a customary manner which is adapted to the use forms.

USE EXAMPLES:

EXAMPLE A

Tetranychus test (OP-resistant)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are strongly infested with all developmental stages of the red spider mite or two-spotted spider mite (*Tetranychus urticae*) are treated by being dipped in the preparation of the active compound of the desired concentration.

After the desired time, the destruction in % is determined. 100% means that all the spider mites have been killed; 0% means that none of the spider mites has been killed.

In this test, the following compounds from the Preparation Examples, for example, exhibit a very strong acaricidal effect: 1, 8, 66, 69 and 70.

TABLE A

Tetranychus test (OP-resistant)
(Plant-damaging mites)

| Active compound | Active compound concentration in % | Degree of destruction in % after 7 days |
|---|---|---|
| 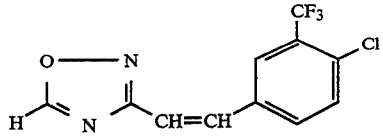 (1) | 0.1<br>0.01 | 100<br>99 |
| 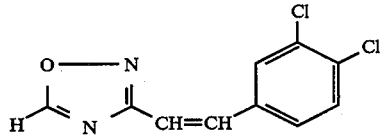 (8) | 0.1<br>0.01 | 98<br>98 |
| 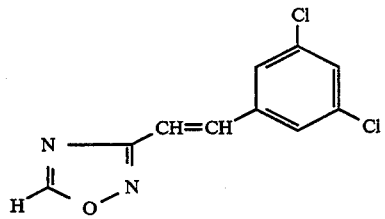 (66) | 0.1<br>0.01 | 98<br>95 |
| 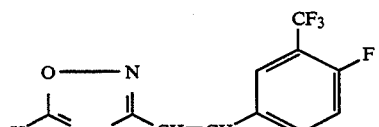 (69) | 0.1<br>0.01 | 98<br>98 |
| 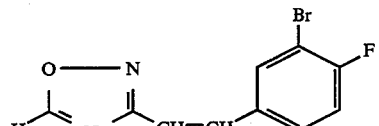 (70) | 0.1<br>0.01 | 100<br>98 |

EXAMPLE B

Phaedon test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage plants (*Brassica oleracea*) are treated with the preparation of the active compound of the desired concentration. One leaf of the treated plant is placed in a plastic box and infested with larvae ($L_3$) of the mustard beetle (*Phaedon cochleariae*). After 2 to 4 days, a further leaf from the same plant is in each case used to provide for continued feeding.

After the desired time, the destruction in % is determined. 100% means that all the animals have been killed; 0% means that none of the animals has been killed.

In this test, the following compounds from the Preparation Examples, for example, exhibit a very strong insecticidal effect: 10, 15 and 57.

TABLE B

Phaedon larvae test
(Plant-damaging insects)

| Active compound | Active compound concentration in % | Degree of destruction in % after 3 days |
| --- | --- | --- |
| Compound (10): oxadiazole with CH=CH linked to 2-F-3-CF₃-phenyl | 0.1<br>0.01 | 100<br>100 |
| Compound (15): oxadiazole with CH=CH linked to 4-OCF₃-phenyl | 0.1<br>0.01 | 100<br>100 |
| Compound (57): isomeric oxadiazole with CH=CH linked to 3,4-difluorophenyl | 0.1<br>0.01 | 100<br>100 |

EXAMPLE C

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the cabbage moth (*Plutella maculipennis*) while the leaves are still moist.

After the desired time, the destruction in % is determined. 100% means that all the caterpillars have been killed; 0% means that none of the caterpillars has been killed.

In this test, the following compounds from the Preparation Examples, for example, exhibit a very strong insecticidal effect: 11, 15, 16 and 57.

TABLE C

Plutella test
(Plant-damaging insects)

| Active compound | Active compound concentration in % | Degree of destruction in % after 3 d |
| --- | --- | --- |
| Compound (11): oxadiazole with CH=CH linked to phenyl bearing OCF₂O ring | 0.1<br>0.01 | 100<br>100 |
| Compound (15): oxadiazole with CH=CH linked to 4-OCF₃-phenyl | 0.1<br>0.01 | 100<br>100 |

TABLE C-continued

Plutella test
(Plant-damaging insects)

| Active compound | Active compound concentration in % | Degree of destruction in % after 3 d |
|---|---|---|
| (16) ![structure with O-N, H-N, C=N, CH=CH, phenyl-S-CF3] | 0.1<br>0.01 | 100<br>100 |
| (57) ![structure with N, H, O-N, CH=CH, phenyl with two F] | 0.1<br>0.01 | 100<br>100 |

EXAMPLE D

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (Oryza sativa) are treated by being dipped into the preparation of the active compound of the desired concentration and infested with the green rice leafhopper (Nephotettix cincticeps) while the seedlings are still moist.

After the desired time, the destruction in % is determined. 100% means that all the leafhoppers have been killed; 0% means that none of the leafhoppers has been killed.

In this test, the following compounds from the Preparation Examples, for example, exhibit a very strong insecticidal effect: 15 and 16.

PREPARATION EXAMPLES:

EXAMPLE 1

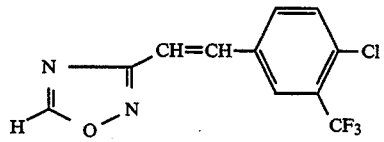

5.2 g (0.02 mol) of (E)-4-chloro-3-trifluoromethylcinnamamide oxime are initially introduced into 50 ml of triethyl orthoformate and 2 drops of boron trifluoride etherate are added at room temperature. The mixture is then stirred at reflux temperature for 2 hours and the whole batch is then concentrated in vacuo. The residue is then taken up in 100 ml of methylene chloride and washed consecutively with 100 ml of 2N hydrochloric acid, saturated sodium carbonate solution and water. The organic phase is dried over sodium sulphate and the solvent is subsequently distilled off. 3.9 g (71.0% of theory) of (E)-3-(4-chloro-3-trifluoromethyl-styryl)-1,2,4-oxadiazole are obtained.

TABLE D

Nephotettix test
(Plant-damaging insects)

| Active compound | Active compound concentration in % | Degree of destruction in % after 6 d |
|---|---|---|
| (15) ![structure O-N, H-N, CH=CH, phenyl-O-CF3] | 0.1<br>0.01 | 100<br>100 |
| (16) ![structure O-N, H-N, CH=CH, phenyl-S-CF3] | 0.1<br>0.01 | 100<br>100 |

M.p.: 85° to 87° C. ¹H NMR (CDCl₃, δ): 7.17; 7.71 (2d, =CH; $J_{H,H}$=16.3 Hz; E form); 7.24–8.70 (3m, arom.); 9.68 (s, =CH) ppm The compounds of the formula (Ia, R¹=H) listed in Table 1 below may be prepared in an analogous manner.

6.4 g (0.03 mol) of (E)-3-chloro-2-fluoro-cinnamamide oxime are initially introduced into 50 ml of acetic anhydride and the mixture is then stirred at reflux temperature for 2 hours. Subsequently, the whole batch is concentrated in vacuo and the residue is stirred with sodium carbonate solution and extracted with methy-

TABLE 1

Examples of the compounds of the formula (Ia)

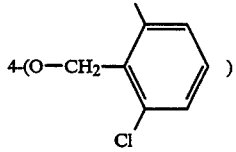

(Ia)

| Ex. No. | R² | R³ | R⁴ | Physical data |
|---|---|---|---|---|
| 2 | —H | 2-Cl | 3-Cl | m.p.: 171–174° C. |
| 3 | —H | 2-F | 3-Cl | m.p.: 95–98° C. |
| 4 | —H | 2-CH₃ | 3-Cl | m.p.: 92–94° C. |
| 5 | —H | 3-CF₃ | 5-CF₃ | m.p.: 102–103° C. |
| 6 | —H | 2-NO₂ | 4-CF₃ | m.p.: 98–100° C. |
| 7 | —H | —H | 4-COOCH₃ | m.p.: 148–151° C. |
| 8 | —H | 3-Cl | 4-Cl | m.p.: 116–118° C. |
| 9 | —H | 2-Cl | 6-Cl | m.p.: 92–93° C. |
| 10 | —H | 2-F | 3-CF₃ | m.p.: 96–98° C. |
| 11 | —H | 3,4-O—CF₂—O— | | m.p.: 113–116° C. |
| 12 | —H | 2-F | 6-Cl | m.p.: 119–121° C. |
| 13 | —H | 2-Cl | 4-Cl | m.p.: 78–80° C. |
| 14 | —H | 2-F | 6-F | m.p.: 64–65° C. |
| 15 | —H | —H | 4-OCF₃ | m.p.: 74–75° C. |
| 16 | —H | —H | 4-SCF₃ | m.p.: 113–114° C. |
| 17 | —H | —H | 4-(O—CH₂—(2,6-dichlorophenyl)) | m.p.: 116–117° C. |
| 18 | —H | —H | 4-(O—CH₂—(4-chlorophenyl)) | m.p.: 168–169° C. |

EXAMPLE 19

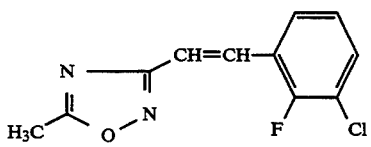

lene chloride. The organic phase is dried over sodium sulphate and the solvent is distilled off. 5.1 g (75.6% of theory) of (E)-3-(3-chloro-2-fluoro-styryl)-5-methyl-1,2,4-oxadiazole are obtained.

M.p.: 95° to 98° C. ¹H NMR (CDCl₃, δ): 2.60 (s, —CH₃); 7.16; 7.76 (2d, =CH; $J_{H,H}$=16.5 Hz; E form); 7.09–7.51 (m, arom.) ppm The compounds of the formula (Ib, R¹=CH) listed in Table 2 below may be prepared in an analogous manner.

TABLE 2

Examples of the compounds of the formula (Ib)

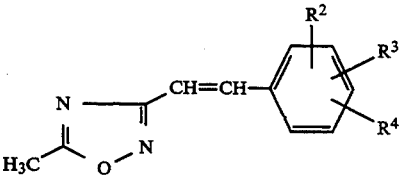

(Ib)

| Ex. No. | R² | R³ | R⁴ | Physical data |
|---|---|---|---|---|
| 20 | —H | —H | 4-OCH₃ | m.p.: 109–110° C. |
| 21 | —H | 2-Cl | 3-Cl | m.p.: 175–179° C. |

TABLE 2-continued

Examples of the compounds of the formula (Ib)

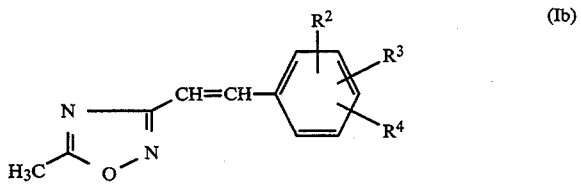

| Ex. No. | R² | R³ | R⁴ | Physical data |
|---|---|---|---|---|
| 22 | —H | 2-CH₃ | 3-Cl | m.p.: 107–108° C. |
| 23 | —H | 3-CF₃ | 5-CF₃ | m.p.: 116–117° C. |
| 24 | —H | —H | 4-COOCH₃ | m.p.: 146–148° C. |
| 25 | —H | 3-F | 4-F | m.p.: 120–121° C. |
| 26 | —H | —H | 4-(O—CH₂—C₆H₄—OCH₃) | m.p.: 159–160° C. |

EXAMPLE 27

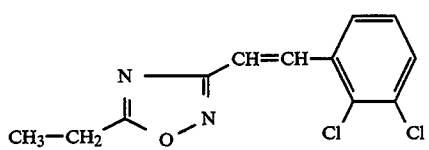

7.0 g (0.03 tool) of (E)-2,3-dichlorocinnamamide oxime are initially introduced into 7 ml of propionic anhydride and the mixture is then stirred at reflux temperature for 2 hours. Subsequently, the whole batch is concentrated in vacuo, and the residue is stirred with sodium carbonate solution and extracted with methylene chloride. The organic phase is dried over sodium sulphate and the solvent is distilled off. 4.7 g (58.2% of theory) of (E) -3- (2,3 -dichloro-styryl) -5-ethyl-1,2,4-oxadiazole are obtained.

M.p.: 107° to 109° C. ¹H NMR (CDCl₃, δ): 1.44 (t, —CH₃; $J_{H,H}=7.6$ Hz); 2.95 (q, —CH₂—; $J_{H,H}=7.6$ Hz); 7.02; 8.07 (2d, =CH; $J_{H,H}=16.0$ Hz); 7.21–7.59 (3m, arom.) ppm The compounds of the formula (Ic, R¹=C₂H₅) listed in Table 3 below may be prepared in an analogous manner.

TABLE 3

Examples of the compounds of the formula (Ic)

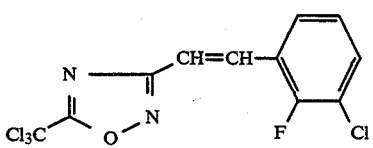

| Ex. No. | R² | R³ | R⁴ | Physical data |
|---|---|---|---|---|
| 28 | —H | —H | 4-OCH₃ | m.p.: 38–40° C. |
| 29 | —H | —H | 4-COOCH₃ | m.p.: 79–80° C. |

EXAMPLE 30

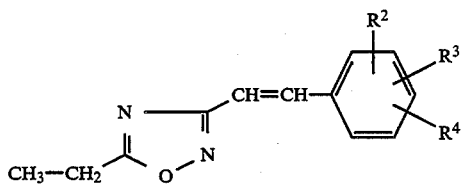

12.7 g (0.07 mol) of trichloroacetyl chloride are added dropwise to a suspension consisting of 6.4 g (0.03 mol) of (E)-3-chloro-2-fluoro-cinnamamide oxime in 90 ml of chloroform and 6 ml (0.07 mol) of dry pyridine. During this process, there is a slight evolution of heat. Subsequently, the mixture is stirred for 1 hour and the pyridine hydrochloride which separates out is filtered off and washed with chloroform. The filtrate is concentrated in vacuo and the remaining solid material is recrystallized. 5.0 g (48.7% of theory) of (E)-3-(3-chloro-2-fluoro-styryl)-5-trichloromethyl-1,2,4-oxadiazole are obtained.

M.p.: 37° to 38° C. ¹H NMR (CDCl₃, δ): 7.12–7.52 (m, arom.+=CH); 7.87 (d, =CH; $J_{H,H}=16.0$ Hz) ppm The compounds of the formula (Id, R¹=CCl₃) listed in Table 4 below may be prepared in an analogous manner.

TABLE 4

Examples of the compounds of the formula (Id)

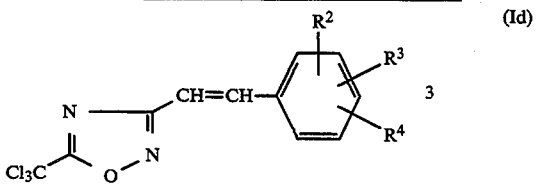

| Ex. No. | R² | R³ | R⁴ | Physical data |
|---|---|---|---|---|
| 31 | —H | —H | 4-OCH₃ | m.p.: 126–129° C. |
| 32 | —H | 3-CF₃ | 5-CF₃ | m.p.: 86–87° C. |

EXAMPLE 33

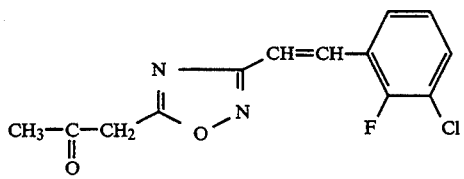

4.3 g (0.02 tool) of (E) -3-chloro-2-fluoro-cinnamamide oxime were initially introduced into 85 ml of toluene and 16.9 g (0.13 mol) of ethyl acetoacetate were then added and the mixture stirred at reflux temperature until the reaction was complete (45 hours). Subsequently, the whole batch is concentrated in vacuo and the remaining residue is recrystallized.

4.3 g (76.6% of theory) of (E) -3- (3-chloro-2-fluorostyryl)-5-(2-oxopropyl)-1,2,4-oxadiazole are obtained as a keto-enol tautomeric mixture (81:19) .

M.p.: 75° to 77° C. $^1$H NMR (CDCl$_3$, δ): 2.15; 2.36 (2s, —CH$_3$); 4.09 (s, —CH$_2$—); 5.56 (s, =CH); 7.18; 7.7; 7.78 (3d, =CH, $J_{H,H}$=16.3 Hz; E form); 7.10–7.51 (m, arom. +=CH); 11.40 (s, —OH) ppm The compounds of the formula (Ie, R$^1$=CH$_2$COCH$_3$) listed in Table 5 below may be prepared in an analogous manner.

TABLE 5

Examples of the compounds of the formula (Ie)

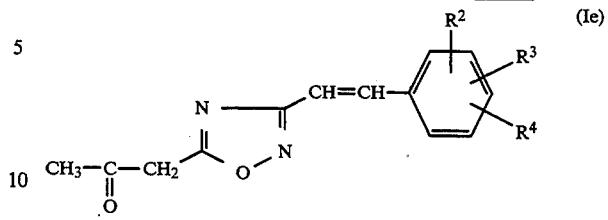

| Ex. No. | R$^2$ | R$^3$ | R$^4$ | Physical data |
|---|---|---|---|---|
| 34 | —H | 2-Cl | 3-Cl | m.p.: 110–112° C. |
| 35 | —H | 3-CF$_3$ | 5-CF$_3$ | m.p.: 122–123° C. |
| 36 | —H | 2-CH$_3$ | 3-Cl | m.p.: 96–97° C. |
| 37 | —H | —H | 4-OCH$_3$ | m.p.: 90–92° C. |

The compounds of the formula (I) listed in Table 6 below, for example, may also be prepared in analogy to Preparation Examples 1, 19, 27, 30 or 33.

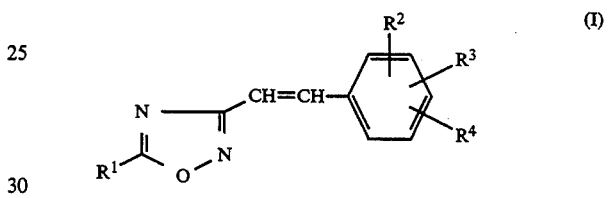

TABLE 6

Examples of the compounds of the formula (I)

| Ex. No. | R$^1$ | R$^2$ | R$^3$ | R$^4$ | Physical data |
|---|---|---|---|---|---|
| 38 | H | H | H | 4-Cl | m.p.: 132–134° C. |
| 39 | H | H | H | H | m.p.: 88–91° C. |
| 40 | H | H | H | 4-OCH$_3$ | m.p.: 87–88° C. |
| 41 | H | H | H | 3-CF$_3$ | m.p.: 46–48° C. |
| 42 | CH$_3$ | H | 4-NO$_2$ | H | m.p.: 182–184° C. |
| 43 | C$_2$H$_5$ | H | 4-NO$_2$ | H | m.p.: 130–131° C. |
| 44 | CH$_3$ | H | H | 3-CF$_3$ | m.p.: 30–31° C. |
| 45 | —CH$_2$—CO—CH$_3$ | H | H | 4-Cl | m.p.: 102–104° C. |
| 46 | —CH$_2$—CO—CH$_3$ | H | H | H | m.p.: 90–91° C. |
| 47 | CCl$_3$ | H | H | H | m.p.: 82–84° C. |
| 48 | CCl$_3$ | H | H | 4-Cl | m.p.: 111–112° C. |
| 49 | CH$_3$ | H | H | 4-Cl | m.p.: 117–118° C. |
| 50 | CH$_3$ | H | H | H | m.p.: 73–75° C. |
| 51 | H | H | H | 2-Cl | m.p.: 54–55° C. |
| 52 | H | H | H | 4-CH(CH$_3$)$_2$ | m.p.: 45–47° C. |
| 53 | CCl$_3$ | H | H | 3-CF$_3$ | m.p.: 49–50° C. |
| 54 | CH$_3$ | H | H | 3-Cl | m.p.: 32–33° C. |
| 55 | H | H | H | 4-CF$_3$ | m.p.: 97–98° C. |
| 56 | H | H | 2-Cl | 3-CF$_3$ | m.p.: 123–125° C. |
| 57 | H | H | 3-F | 4-F | m.p.: 98–99° C. |
| 58 | H | H | 2-F | 3-CH$_3$ | m.p.: 40° C. |
| 59 | H | H | 3-CH$_3$ | 4-OCH$_3$ | m.p.: 91–92° C. |
| 60 | H | H | 2-F | 3-F | m.p.: 104–105° C. |
| 61 | H | H | 3,4-O—CH$_2$—O— | | m.p.: 147–150° C. |
| 62 | H | H | 2-CH$_3$ | 4-CH$_3$ | m.p.: 73–74° C. |
| 63 | H | H | 2-OCH$_3$ | 3-OCH$_3$ | m.p.: 55–57° C. |
| 64 | H | H | 3-Cl | 4-OCF$_2$CHFCF$_3$ | m.p.: 31–34° C. |
| 65 | CH$_3$ | H | 2-F | 3-F | m.p.: 115–116° C. |
| 66 | H | H | 3-Cl | 5-Cl | m.p.: 144–145° C. |
| 67 | H | H | 3-Cl | 4-CF$_3$ | m.p.: 99–100° C. |
| 68 | H | H | 3-Cl | 4-OCF$_3$ | m.p.: 57–58° C. |
| 69 | H | H | 4-F | 3-CF$_3$ | m.p.: 78–79° C. |
| 70 | H | H | 3-Br | 4-F | m.p.: 123–125° C. |
| 71 | H | H | 3-Br | 4-OCH$_3$ | m.p.: 137–138° C. |
| 72 | H | H | H | 3-SCF$_3$ | m.p.: 89° C. |

TABLE 6-continued

Examples of the compounds of the formula (I)

| Ex. No. | R¹ | R² | R³ | R⁴ | Physical data |
|---|---|---|---|---|---|
| 73 | H | H | H | 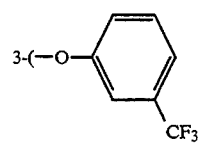 3-(—O— ... CF₃) | m.p.: 49–50° C. |
| 74 | —CF₂CF₃ | H | 3-Cl | 4-Cl | m.p.: 49–51° C. |
| 75 | 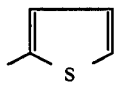 | H | 3-Cl | 4-Cl | m.p.: 180–181° C. |
| 76 | CF₃ | H | 3-Cl | 4-Cl | m.p.: 87–89° C. |
| 77 | CF₂Cl | H | 3-Cl | 4-Cl | m.p.: 72–73° C. |
| 78 | H | H | 3-Cl | 4-F | m.p.: 138–138° C. |
| 79 | H | H | 3-O—CH₂CH₂—O-4 | | m.p.: 80° C. |
| 80 | CCl₃ | H | 3-Cl | 4-Cl | m.p.: 124–126° C. |
| 81 | H | H | 2-CH₃ | 3-C₆H₅ | m.p.: 109–110° C. |
| 82 | H | H | 2-CH₃ | 4-N(CH₃)₂ | m.p.: 145–146° C. |
| 83 | H | H | 2-CH₃ | 3-CF₃ | m.p.: 103–105° C. |
| 84 | H | 2-F | 3-Cl | 4-F | m.p.: 99–100° C. |
| 85 | H | H | H | 2-C₆H₅ | m.p.: 71–73° C. |
| 86 | 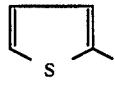 | H | 2-F | 3-Cl | m.p.: 125–126° C. |
| 87 | 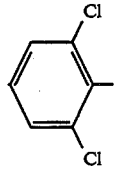 | H | 2-F | 3-Cl | m.p.: 133–135° C. |
| 88 | H | H | 3-OCH₃ | 4-OCH₃ | m.p.: 105–107° C. |
| 89 | CH₂CH(CH₃)₂ | H | 2-F | 3-Cl | m.p.: 45–47° C. |
| 90 | 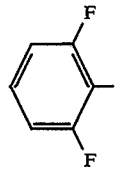 | H | 2-F | 3-Cl | m.p.: 148–149° C. |
| 91 | 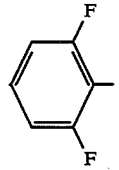 | 2-OCH₃ | 3-OCH₃ | 4-OCH₃ | m.p.: 123–124° C. |
| 92 | H | 3-OCH₃ | 4-OCH₃ | 5-OCH₃ | m.p.: 128–130° C. |
| 93 | H | H | 2-O—CF₂—CHF—O-3 | | m.p.: 136° C. |
| 94 | CCl₃ | 3-OCH₃ | 4-OCH₃ | 5-OCH₃ | m.p.: 104–105° C. |
| 95 | CCl₃ | H | 2-OCF₂—CHF—O-3 | | m.p.: 93–95° C. |
| 96 | H | H | 3-CH₂—CH₂—C(CH₃)₂—O-4 | | m.p.: 87–88° C. |
| 97 | 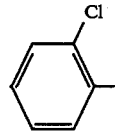 | H | 2-F | 3-Cl | m.p.: 134–135° C. |

TABLE 6-continued

Examples of the compounds of the formula (I)

| Ex. No. | R¹ | R² | R³ | R⁴ | Physical data |
|---|---|---|---|---|---|
| 98 | 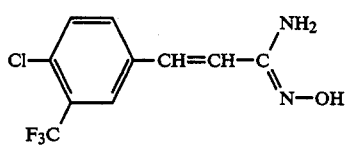 | H | 2-F | 3-Cl | m.p.: 128–130° C. |
| 99 | (2,3-dichlorophenyl) | H | 2-F | 3-Cl | m.p.: 154–156° C. |

STARTING COMPOUNDS OF THE FORMULA (II)

EXAMPLE (II-1)

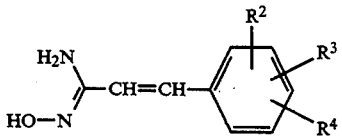

12.1 g (0.05 mol) of 4-chloro-3-trifluoromethylcinnamonitrile are added to a solution consisting of 7.2 g (0.10 mol) of hydroxylamine hydrochloride and 7.3 g (0.10 mol) of sodium carbonate in 100 ml of water and 100 ml of ethanol. The mixture is heated at reflux temperature until the reaction is complete (24 hours) and the whole batch is subsequently stirred into 250 ml of water. The solid material which separates off during this process is filtered off with suction, washed with a little water and dried. 5.3 g (39.3% of theory) of (E)-4-chloro-3-trifluoromethylcinnamamide oxime are obtained.

M.p.: 135° to 137° C. ¹H NMR (CDCl₃, δ): 5.64 (br s, —NH₂); 6.60; 7.15 (2d, =CH; $J_{H,H}$=16.5 Hz; E form); 7.68–10.00 (m, arom.); 11.89 (s, —OH) ppm The compounds of the formula (II) listed in Table 7 below may be prepared in an analogous manner.

TABLE 7

Starting compounds of the formula (II)

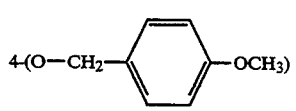

(II)

| Ex. No. | R² | R³ | R⁴ | Physical data |
|---|---|---|---|---|
| II-2 | —H | 2-F | 3-CF₃ | 5.75; 9.97 a) |
| II-3 | —H | 3-Cl | 4-Cl | 5.60; 9.92 a) |
| II-4 | —H | 2-Cl | 6-F | 5.74; 9.93 a) |
| II-5 | —H | 2-F | 6-F | m.p.: 165–166° C. |
| II-6 | —H | —H | 4-OCF₃ | 5.63; 9.84 a) |
| II-7 | —H | —H | 4-SCF₃ | 5.68; 9.94 a) |
| II-8 | —H | 2-Cl | 3-CF₃ | 4.93; 8.62 b) |
| II-9 | —H | 3-CH₃ | 4-OCH₃ | 5.55; 9.66 a) |
| II-10 | —H | 3,4-O—CF₂—O— | | 5.58; 9.00 E Form a) 5.33; 11.52 Z Form a) |
| II-11 | —H | 3,4-O—(CH₂)₂—O— | | 5.52; 9.65 a) |
| II-12 | —H | —H | 4-(O—CH₂—C₆H₄—OCH₃) | 5.54; 9.64 a) | a) ¹H NMR (DMSO d₆, δ, ppm);
b) ¹H NMR (CDCl₃, δ, ppm); in each case singlets (broad) for

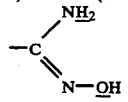

Example of the preparation of the cinnamonitriles employed as precursors (cf., e.g., Foucaud et al. Synthesis (1979), pp. 884 to 885):

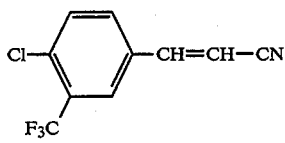

A solution consisting of 10.6 g (0.06 mol) of diethyl cyanomethylphosphonate and 12.5 g (0.06 mol) of 4-chloro-3-trifluoromethylbenzaldehyde in 65 ml of tetrahydrofuran is added dropwise to a suspension of 6.7 g (0.12 mol) of powdered potassium hydroxide in 185 ml of tetrahydrofuran. During this process, there is a slight evolution of heat. Subsequently, the mixture is stirred at room temperature for 20 minutes and the solid material which separates off is filtered off and washed with tetrahydrofuran. The filtrate is concentrated in vacuo and the remaining residue is dried. 12.1 g (87.0% of theory) of 4-chloro-3-trifluoromethyl-cinnamonitrile are obtained as an E/Z isomeric mixture.

M.p.: 89°–92° C. $^1$H NMR (CDCl$_3$, δ): 5.60; 7.13 (2d, =CH, $J_{H,H}$=12 Hz; Z form); 5.96; 7.38 (2d, =CH, $J_{H,H}$=16.5 Hz; E form); 7.57–8.07 (m, arom.) ppm The compounds listed in Table 8 below may be prepared in an analogous manner:

TABLE 8

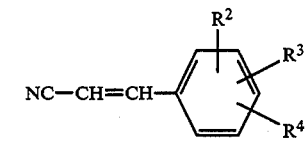

| Ex. No. | R$^2$ | R$^3$ | R$^4$ | Physical data |
|---|---|---|---|---|
| a | —H | 2-F | 3-CF$_3$ | 6.11; 7.53 E-Form a) 5.71; 7.45 Z-Form |
| b | —H | 3-Cl | 4-Cl | 5.89; 7.30 E-Form a) |
| c | —H | 2-Cl | 6-F | 5.89; 7.75 E-Form a) 5.62; Z-Form |
| d | —H | 2-F | 6-F | 6.25; 7.46 E-Form a) 5.80; 7.14 Z-Form |
| e | —H | —H | 4-OCF$_3$ | 5.87; 7.39 E-Form a) 5.51; 7.13 |
| a | —H | 2-F | 3-CF$_3$ | 6.11; 7.53 E Form a) 5.71; 7.45 Z Form |
| b | —H | 3-Cl | 4-Cl | 5.89; 7.30 E Form a) |
| c | —H | 2-Cl | 6-F | 5.89; 7.75 E Form a) 5.62; Z Form |
| d | —H | 2-F | 6-F | 6.25; 7.46 E Form a) 5.80; 7.14 Z Form |
| e | —H | —H | 4-OCF$_3$ | 5.87; 7.39 E Form a) 5.51; 7.13 |
| f | —H | —H | 4-SCF$_3$ | 5.99; 7.44 E Form a) |
| g | —H | 2-Cl | 3-CF$_3$ | 5.95; 7.91 E Form a) 5.74; 7.61 Z Form |
| h | —H | 3-CH$_3$ | 4-OCH$_3$ | 5.70; 7.30 E Form a) 5.25; 7.00 Z Form |
| i | —H | 3,4-O—CF$_2$—O— | | 5.81; 7.35 E Form a) 5.47; Z Form |
| j | —H | 3,4-O—(CH$_2$)$_2$—O— | | 5.69; 7.28 E Form a) 5.29; Z Form |
| k | —H | —H | 4-(O—CH$_2$—⌬—OCH$_3$) | 5.71; E Form a) | a) $^1$H NMR (CDCl$_3$, δ, ppm); in each case doublets ($J_{H,H}$ = 16.5 Hz; E form) and ($J_{H,H}$ = 12.0 Hz; Z form) for —CH=CH—

We claim:
1. A method for controlling plant-parasitic insects or mites which comprises applying to such insects or mites or their habitat an amount effective to control such insects or mites of at least one substituted, 1,2,4-oxadiazole derivative of the formula (I)

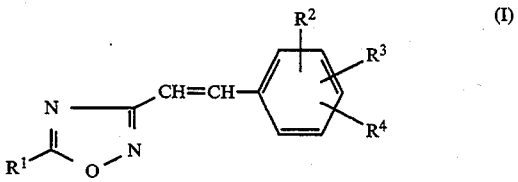

in which
R$^1$ represents hydrogen, or represents in each case optionally substituted alkyl, cycloalkyl, aryl or heterocyclyl,
R$^2$ represents hydrogen, nitro, cyano, carboxyl, carbamoyl or halogen, or represents in each case optionally substituted alkyl, alkoxy or alkylthio,
R$^3$ represents hydrogen, nitro, cyano, carboxyl, carbamoyl or halogen, or represents in each case optionally substituted alkyl, alkoxy or alkylthio, and
R$^4$ represents hydrogen, hydroxyl, mercapto, amino, halogen, alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, alkylamino, dialkylamino, alkylcarbonylamino, alkylcarbonyl, alkylcarbonyloxy, alkoxycarbonyl, alkoxyalkyl, hydroxyalkoxy or alkoyalkoxy, or represents aryl, aryloxy, aralkyloxy arylthio, aralkylthio, arylsulphinyl or arylsulphonyl, which are in each case optionally substituted by halogen, alkyl, halogenoalkyl, alkoxy or halogenoalkoxy, or, together with $R^3$, represents alkanediyl, alkylene (di) oxy or halogenoalkylenedioxy.

2. The method according to claim 1, characterized in that in the formula (I)

$R^1$ represents hydrogen, or represents straight-chain or branched alkyl having 1 to 6 carbon atoms, which is optionally substituted by hydroxyl, halogen, $C_3$-$C_6$-cycloalkyl, $C_1$-$C_6$-alkoxy, $C_1$-$C_4$-alkyl-carbonyl, $C_1$-$C_4$-alkoxycarbonyl or phenyl, or represents $C_3$-$C_6$-cycloalkyl or phenyl, which are in each case optionally substituted by halogen or $C_1$-$C_4$-alkyl, or represents pyridyl, furyl or thienyl, $R^2$ represents hydrogen, nitro, cyano, carboxyl, carbamoyl or halogen, or represents alkyl, alkoxy or alkylthio having in each case 1 to 4 carbon atoms, which are in each case optionally substituted by halogen, $R^3$ represents hydrogen, nitro, cyano, carboxyl, carbamoyl or halogen, or represents alkyl, alkoxy or alkylthio having in each case 1 to 4 carbon atoms, which are in each case optionally substituted by halogen, and $R^4$ represents hydrogen, hydroxyl, mercapto, amino or halogen, or represents alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphinyl, alkylamino, dialkylamino, alkylcarbonylamino, alkylcarbonyl, alkylcarbonyloxy, alkoxycarbonyl, alkoxyalkyl, hydroxyalkoxy or alkoxyalkoxy having in each case 1 to 4 carbon atoms, or represents phenyl, phenoxy, benzyloxy, phenylthio, benzylthio, phenylsulphinyl or phenylsulphonyl, which are in each case optionally substituted by halogen, $C_1$-$C_4$-alkyl, $C_1$-$C_4$-halogenoalkyl, $C_1$-$C_4$-alkoxy or $C_1$-$C_4$-halogenoalkoxy, or, together with $R^3$, represents $C_3$-$C_4$-alkanediyl, $C_1$-$C_3$-alkylene(di)oxy or $C_1$-$C_2$-halogenoalkylenedioxy.

3. The method according to claim 1, characterized in that in the formula (I)

$R^1$ represents hydrogen, or represents straight-chain or branched $C_1$-$C_4$-alkyl, which is optionally substituted by fluorine, chlorine, bromine, methoxy, ethoxy, acetyl, propionyl, methoxycarbonyl or ethoxycarbonyl, or represents cyclopropyl, cyclopentyl, cyclohexyl or thienyl, $R^2$ represents hydrogen, nitro, cyano, fluorine, chlorine or bromine, or represents alkyl, alkoxy or alkylthio having in each case 1 to 4 carbon atoms, which are in each case optionally substituted by fluorine and/or chlorine, $R^3$ represents hydrogen, nitro, cyano, fluorine, chlorine or bromine, or represents alkyl having 1 to 4 carbon atoms, which is in each case optionally substituted by fluorine and/or chlorine, and $R^4$ represents hydrogen, fluorine, chlorine, bromine, methyl, ethyl, trifluoromethyl, chlorodifluoromethyl, fluorodichloromethyl, methoxy, ethoxy, difluoromethoxy, trifluoromethoxy, methylthio, ethylthio, difluoromethylthio, trifluoromethylthio, chlorodifluoromethylthio, fluorodichloromethylthio, methylsulphinyl, ethylsulphinyl, trifluoromethylsulphinyl, methylsulphonyl, ethylsulphonyl, trifluoromethylsulphonyl, methylamino, ethylamino, dimethylamino, acetylamino, acetyl, acetyloxy, methoxycarbonyl or ethoxycarbonyl, or represents phenyl, phenoxy or benzyloxy, which are in each case optionally substituted by fluorine, chlorine, bromine, methyl, trifluoromethyl, methoxy or trifluoromethoxy, or, together with $R^3$, represents $C_1$-$C_2$-alkylenedioxy which is optionally substituted by fluorine and/or chlorine.

* * * * *

UNITED STATES PATENT AND TRADEMARK OFFICE
CERTIFICATE OF CORRECTION

PATENT NO. : 5,428,049
DATED : June 27, 1995
INVENTOR(S) : Jeschke, et al.

It is certified that error appears in the above-indentified patent and that said Letters Patent is hereby corrected as shown below:

Col. 25, line 2    Delete " alkoyalkoxy " and substitute
                   -- alkoxyalkoxy --

Col. 25, line 34   Delete " halogenoalkylsulphinyl " and
                   substitute -- halogenoalkylsulphonyl --

Signed and Sealed this

Nineteenth Day of September, 1995

Attest:

BRUCE LEHMAN

*Attesting Officer*                *Commissioner of Patents and Trademarks*